(12) United States Patent
Gavronsky et al.

(10) Patent No.: US 7,200,444 B2
(45) Date of Patent: Apr. 3, 2007

(54) METHOD AND DEVICE FOR ELECTRO-ACUPUNCTURE

(76) Inventors: Stas Gavronsky, 39 Wayland Hills Rd., Wayland, MA (US) 01778; Mark Gerlovin, 7134 Lexington Ridge Dr., Lexington, MA (US) 02421

( * ) Notice: Subject to any disclaimer, the term of this patent is extended or adjusted under 35 U.S.C. 154(b) by 370 days.

(21) Appl. No.: 10/962,299

(22) Filed: Oct. 9, 2004

(65) Prior Publication Data
US 2006/0079946 A1    Apr. 13, 2006

(51) Int. Cl.
*A61N 1/36* (2006.01)
(52) U.S. Cl. .......................... 607/46; 128/907; 607/63; 607/2; 607/115; 607/116; 606/41
(58) Field of Classification Search .................. 607/46, 607/63, 115, 116, 142, 149, 152; 606/41; 128/907; 600/372, 382, 386, 548
See application file for complete search history.

(56) References Cited
U.S. PATENT DOCUMENTS

| | | | | |
|---|---|---|---|---|
| 4,317,458 | A | * | 3/1982 | Yokoyama .................. 607/122 |
| 5,324,287 | A | * | 6/1994 | Szeles ........................ 606/41 |
| 6,004,304 | A | * | 12/1999 | Suzuki et al. ............... 604/272 |
| 6,549,810 | B1 | | 4/2003 | Leonard |
| 6,701,190 | B2 | | 3/2004 | Gliner |
| 7,120,499 | B2 | * | 10/2006 | Thrope et al. ................ 607/48 |

2004/0044390 A1 * 3/2004 Szeles ........................ 607/142

OTHER PUBLICATIONS

U.S. Appl. No. 10/068,826, Stas Gavronsky.
Transcutaneous Electrical Nerve Stimulation. Author: V. Kaye, et. al. (http:www.ycyhealth.com/tens/Literature/tens_Vladimir.shtml).
APS Bulletin. Mar./Apr. 1999, V. 9, No. 2 Percutaneous Electrical Nerve Stimulation (PENS); A Promising Alternative—Medicine Approach to Pain Management. By P. White, et al.
American Journal of Pain Management, vol. 12, No.; By Ong and Ho, (Article).

* cited by examiner

*Primary Examiner*—Kennedy Schaetzle (57) ABSTRACT

The present invention provides a principally novel method and a device for percutaneous electrical nerve stimulation and electro-acupuncture. It consists of inserting the needles/electrodes into the prescribed acupuncture/trigger points at slant angles so that the external parts of the needles/electrodes can be secured against the skin of the patient. Although the present method allows for usage of different types of percutaneous electrodes and perpendicular insertions, as long as the external parts of electrodes are in flush with the patient's skin, angular insertion of the needles/electrodes has significant advantages. First, the inclined position of the needle provides distribution of current over a larger area of the patient's skin since the inserted part of the needle is longer in the inclined position that in the perpendicular position. Second, as the projecting part of the needle is secured to the surface of the skin, a patient is not restrained by the needles and may have freedom of motion. In other words, after insertion of the needles the patient may leave the clinic and may not be bound to the clinic during subsequent usage of the device.

31 Claims, 6 Drawing Sheets

METHOD AND DEVICE FOR ELECTRO-ACUPUNCTURE

CROSS-REFERENCE TO RELATED APPLICATIONS

The present patent application is related to U.S. patent application Ser. No. 10/068,826, now U.S. Pat. No. 6,836,686, filed by the same applicant on Feb. 11, 2002 and entitled "Electro-acupuncture device".

FEDERALLY SPONSORED RESEARCH

Not Applicable

SEQUENCE LISTING OR PROGRAM

Not Applicable

BACKGROUND OF THE INVENTION

1. Field of Invention

The present invention relates to the field of electrical therapy for treating pain and other conditions, in particular to electro-acupuncture and percutaneous electrical nerve stimulation therapy. The present invention is more specifically directed to a method and device capable of delivering continuous pain relief through percutaneous nerve stimulation both in and out of clinic.

2. Prior Art

Electrical therapy has long been used in medicine to treat pain and other conditions. One of the forms of electrical therapy is Transcutaneous Electrical Nerve Stimulation (TENS). The TENS method is based on a hypothesis of Melzack and Wall from 1965. They proposed that activity in coarse, afferent nerve fibers (A-beta-fibers that convey pressure, touch, and vibration) inhibits impulse transmission in pain pathways at spinal cord level. The coarse nerve fibers have a low threshold for electrical stimulation and are therefore simple to activate by stimulation using electrodes placed on the skin. Usually stimulation frequencies of 20–120 Hz are used for conventional TENS. Electro-acupuncture is another example of electrical therapy, which has been used successfully for a number of years. Current U.S. patent application Ser. No. 10/068,826 submitted by the same applicant on Feb. 11, 2002 describes an improved electro-acupuncture device.

In recent years, Percutaneous Electrical Nerve Stimulation (PENS) has been used and investigated for the management of acute and chronic pain syndromes. PENS is a new analgesic therapy that combines advantages of both electro-acupuncture and TENS. PENS therapy utilizes acupuncture-like electrodes placed in the soft tissues to stimulate peripheral sensory nerves at the dermatomal level corresponding to a local pathology. TENS, on the other hand, is a procedure that involves electrical stimulation on the surface of the skin through cutaneous electrode pads. Electro-acupuncture is similar to PENS except that it is influenced by acupuncture theory of the meridians, energy channels, and their distribution for a choice of sites to be stimulated with electricity. In modern medical acupuncture stimulation sites are chosen from both meridian and neurological considerations. A difference between PENS and TENS electro-acupuncture from the physiological perspective is well described in the American Journal of Pain Management Vol. 12 No. 4 by Ong and Ho. The article shows differences and similarities in mechanisms of pain interruption between TENS and acupuncture/electro-acupuncture along the ascending nociceptive pathways, namely, at peripheral, spinal segmental, supraspinal, and cortical levels. On peripheral level electro-acupuncture stimulates mainly the pinprick Adelta and small type III fibers for its effect.

TENS stimulates mainly the tactile Abeta and large type I fibers for its effect. On the spinal level electro-acupuncture's effect is mediated via the inhibitory enkephalinergic stalked cells in lamina II of the spinal grey matter. TENS's effect is mediated via interneurons with GABA receptors in the spinal cord and this stimulates the inhibitory neurons. On the supraspinal level electro-acupuncture activates pituitary mechanisms releasing enkephalins and produces analgesia throughout the body. Conventional TENS are mostly segmental not involving pituitary mechanisms, and the analgesic effect is only segmental.

In clinic both electro-acupuncture and PENS seem to be significantly more effective than TENS. Ghoname and colleagues conducted a randomized, controlled, crossover study to compare effectiveness of PENS, TENS, and exercise therapy in 60 patients with chronic low back pain secondary to degenerative disc disease. The authors described the PENS as a therapy that combines the advantages of TENS and those of electro-acupuncture. Compared with sham PENS, TENS and exercise therapy, PENS was more effective in improving function, pain, physical activity, and quality of sleep. PENS therapy was preferred by 91% of the patients.

PENS therapy has been found to be effective in the management of pain associated with a number of conditions, including acute herpes zoster (Ahmed, Craig, White, Ghoname et al., 1998), the prevention and treatment of migraine headaches after electroconvulsive therapy, cancer pain secondary to bone metastases (Ahmed, Craig, White, & Huber, 1998). Compared with dorsal column stimulation, the PENS technique is less invasive, less costly, and less risk ridden. Electro-acupuncture has been also found effective for many conditions including, but not limited to, Irritable Bowel Syndrome and dysmenorrhea.

Currently, a PENS procedure is performed in clinic by a pain specialist, typically, by physiatrist, anesthesiologist, or acupuncturist. Patient is usually prone on the treatment table, when two or more needles/electrodes are inserted in the back and around the spine according to the location of pain. Electrodes are kept in place for 30 min to 1 hour, while being stimulated with alternating electrical current generator at frequencies typically from several to 100 Hz. Since the electrical resistance of the skin is short-circuited by the inserted electrodes, and the actual electrical current through the electrodes is very small (in milli-amperes range), the electrical stimulator can operate for a long time from a single 9V battery. These electrical devices are currently available as electro-acupuncture machines. They offer variable frequencies, intensities, and one or multiple outputs. Needle electrodes are inserted perpendicular to the skin at variable depths, depending on the area, patient's anatomy, and the etiology of pain, anywhere from several millimeters to several centimeters. Electrical clips with electrical wires are attached to the electrodes before the electrical stimulator is turned on. An example of the improved electrodes can be found in aforementioned U.S. patent application Ser. No. 10/068,826 field by one of the Applicants of the present application on Feb. 11, 2002. There have been many attempts to improve the electrodes and to find ideal stimulating modes (frequencies and intensities) for PENS in prior arts. Examples can be found in U.S. Pat. No. 6,549,810 issued to Paul Leonard et al. in 2003 and U.S. Pat. No. 6,701,190 issued to Brad Gliner in 2004.

While there are some differences in electrode design, duration of the procedure, and frequency modes between PENS procedures, several characteristics have remained the same in all prior arts. Namely, electrodes/needles are inserted perpendicular to the body and the external parts of the electrodes protrude above the skin. The patient has to be stationary on the table during the duration of the procedure, for 30 to 60 minutes. Also, treatment can be only repeated during patient's next visit to a pain clinic.

Objects and Advantages

It is an object of present invention to provide a principally different method and a device for percuteneous electrical nerve stimulation and electro-acupuncture which are safer, less expensive, easy in use, and provide a patient with a higher level of control over his/her pain than known devices and methods of similar type. It is another object of the invention to provide the aforementioned method and device that allow positioning of the non-inserted external part of the needles/electrodes in flush with the patient's skin so that the this part does not project perpendicular to the patient's skin. It is another object to provide the aforementioned device that allows a patient to have freedom of movements so that the patient is not bound to the clinic during prolonged usage of the device.

SUMMARY

The present invention provides a principally novel method and a device for percutaneous electrical nerve stimulation and electro-acupuncture. It consists of inserting the needles/electrodes into the prescribed acupuncture/trigger points at slant angles so that the external parts of the needles/electrodes can be secured against the skin of the patient. Although the present method allows for usage of different types of percutaneous electrodes and perpendicular insertions, as long as the external parts of electrodes are in flush with the patient's skin, angular insertion of the needles/electrodes has significant advantages. First of all, a needle/electrode, which is inserted into the area of interest at a slant angle, has a greater portion of its shaft embedded into the tissue when compared with a perpendicularly inserted needle that reaches a point on the same depth. Thus, the electrical current, which emanates from the embedded part of the needle, is distributed over the length of that part. A patient much better tolerates the same amount of electricity, but with a lesser density that results from such distribution, since it does not produce an unpleasant "pinching" sensation. Second of all, the distributed current is spread over a larger area of the patient's skin and tissue and thus stimulates a greater number of afferents than a localized current. For example, two angularly inserted needles/electrodes can be positioned inside the muscle tissue at some distance and parallel to each other while their embedded shafts can be oriented across muscular fibers. In that case, broad muscle area can be percutaneously stimulated with electricity. In some areas, say abdomen, deep perpendicular insertions are not allowed, since a needle should not enter the abdominal cavity. The only way to have a needle/electrode well secured on the abdomen for a prolonged PENS usage at home is to embed the shaft of the electrode subcutaneously at the sharp angle. Gastric dysrhythmias and Irritable Bowel Syndrome are examples of the conditions that are ideally suited for the treatment with the aforementioned method and device.

After at least two needles/electrodes are inserted and positioned according to the above-described principals, their external parts/handles are secured against the patient's skin and are brought in contact with the conductive pads. First, the insulator pads are attached to the skin via their adhesive layers. Each insulator pad has an opening in the middle. The insulator pad covers the area where the needle/electrode is inserted, but allows the external portion of the needle/electrode to be accessible through the opening in the pad. Then, the conductive pad, which is encapsulated within protecting insulating covering on all sides except the bottom where it is treated with conductive adhesive gel, is placed on top of the insulator pad. It gets in contact with the needle/electrode via the opening in the insulator pad. An insulator pad can be integrated with the conductive pad and can cover the contact surface of the conductive pad along the periphery. The insulator pad protects skin from electrical contact with the conductive pad and improves comfort of the patient by minimizing area in contact with conductive gel. Electrical wires, then, connect conductive pads with portable PENS generator. The PENS generator normally generates an alternating electrical current of a pre-determined frequency (usually 2 to 100 Hz). This current flows through the electrical wires, conductive pads, into the needles/electrodes, and through the tissues located between two needles/electrodes. Essentially, the tissues that are located between the related electrodes of each pair represent he electrical load for the PENS generator. PENS generator can have multiple outputs and be capable of stimulating more than one pair of needle/electrodes and the areas between the needles of each pair. Portable PENS device can be worn on the patient's body under the cloth for a prolonged period of time. Portable electrical device is capable of providing multiple therapeutic PENS sessions in a course of one day for the same patient in order to control pain without extra participation of a health care provider. The number of the therapeutic sessions and their modes, such as the intensity of the electrical current, frequency, and duration of each session can be pre-programmed by a therapist or controlled manually by the patient according to the patient's needs.

In one of the embodiment of the invention, the needle has a handle portion perpendicular to the insertable part of the needle, so that when the insertable part is inserted into the patient's skin to its full length, the external handle portion is arranged parallel to the patient's and rests onto the patient's skin. Thus, no part of the needle projects perpendicular to the patient's skin so that the main objective of the invention that a patient is not restrained by the needles and may have freedom of motion is accomplished.

REFERENCE NUMERALS

20—electrode assembly
20a, 20b—electrode assemblies
22—conductive pad
22a—lower surface of the conductive pad 22
24—insulating covering
26—insulating pad
26a—adhesive layer
28—adhesive layer
30—needle/electrode
30a—conductive needle body
30b—conductive needle head
32—adhesive gel
34—lead wire
34a, 34b—lead wires
40a, 40b, 40c, 40d—output terminals of the pulse generator—
40—PENS generator
40a, 40b—output terminal of the PENS generator
42—generator unit
44a, 44b—current-controlled bi-phasic outputs
46—control unit
48—power source
50—transmitter
52—RF receiver
54—tensor meter
56—insulation pad
58—lead wire
60—needle
62, 64—conductive pads
68, 70—needles
72—insulating pad
74—sealing pad
76—electrode assembly
77—adhesive layer
78—PENS generator
80, 82—lead wires
84, 86—primary coils
88, 90—secondary coils
92, 94—lead wires
96—enclosure
98, 100, 102, 104—electrode assemblies
106—PENS generator
108—remote control
α—angle of the needle to the patient's skin
h—height of the electrode assembly over the patient's skin
S—patient's skin

DETAILED DESCRIPTION—PREFERRED EMBODIMENT

Figure 1:
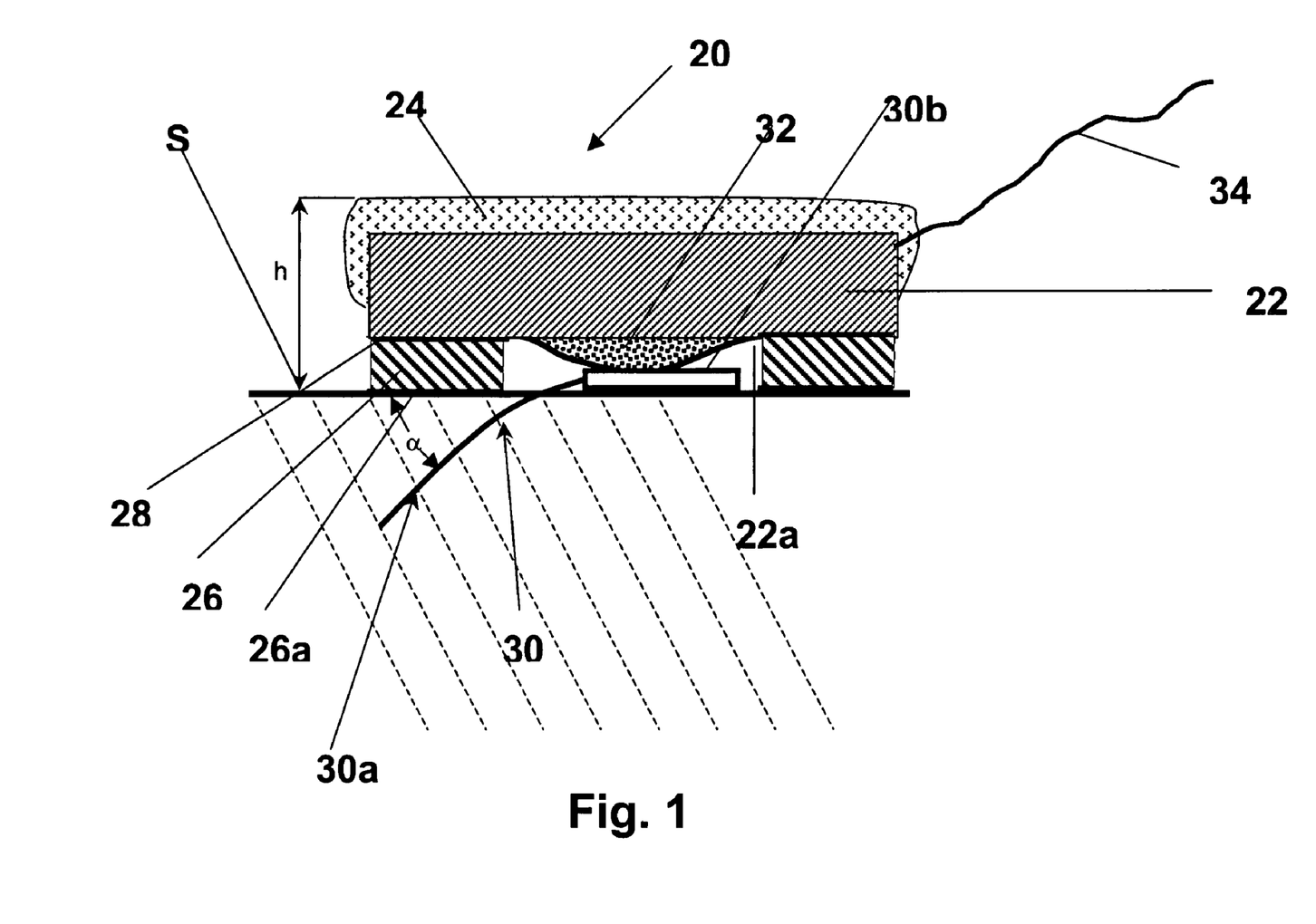
FIG. 1 is a sectional general view of an electrode assembly of the invention that illustrates the position of a needle/electrode relative to the patient's skin.

FIG. 1 is a general view of an electrode assembly of the invention that illustrates the position of a needle/electrode relative to the patient's skin. The electrode assembly, which in general is designated by reference numeral 20, consists of a conductive pad 22 covered by a protective insulating covering 24 and is attached to the patient's skin S via an insulating pad 26. In case when the electrode assembly is circular in shape, the insulating pad 26 has a shape of a flat ring. The insulating pad 26 is rigidly attached to the conductive pad 22, e.g., via a respective adhesive layer 28 and can be attached to the patient's skin S by means of an adhesive layer 26a.

A needle/electrode 30 possesses flexibility and is made of a conductive material, e.g., steel, silver, etc, and consists of a conductive needle body 30a and a conductive needle head 30b. The needle/electrode 30 is inserted into the patient's skin S at an acute angle α to the surface of the skin S. Depending on flexibility of the needle material, depth of penetration into the patent's skin S, the length of the over-the-skin portion of the needle/electrode, and other circumstances, angle α may vary, e.g., from 5° to 45°. The needle head 30b is kept pressed against the patient's skin in flash with the skin surface by means of a layer of a conductive adhesive gel 32 placed between the needle head 30b and the lower surface 22a of the conductive pad 22. In FIG. 1, reference numeral 34 designates a lead wire that connects the conductive pad 22 with a PENS generator 38 shown in FIG. 2, which is a block diagram of the entire electro-acupuncture apparatus or system according to one embodiment of the invention.

In the embodiment shown in FIG. 2, the acupuncture apparatus of the invention contains a pair of electrode assemblies 20a and 20b of the same type as the one that has been described with reference to FIG. 1. Both assemblies 20a and 20b are identical. Reference numeral 40 designates a PENS generator 40, which is connected to the respective electrode assemblies by lead wires 34a and 34b. The lead wire 34a connects the conductive pad 24a to an output terminal 40a of the PENS generator 40, while the lead wire 34b connects the conductive pad 24b to the second output terminal 40b of the PENS generator 40. Multiple pairs of electrodes that can be used are limited only by the number of PENS generator's outputs.

The PENS generator may be a commercially available product and in general may consists of a pulse generator unit 42 (FIG. 2) that may have a set of output terminals 40a, 40b, 40c, 40d, . . . (only two of which 40a and 40b are used in the embodiment of FIG. 2) connected to the pulse generator unit 42 via respective current-controlled bi-phasic outputs 44a, 44b, . . . . The pulse generator 42 is controlled from a control unit. Reference numeral 48 designates a power source of the generator 42 and control unit 46. The pulse generator assembly 40 may be remotely controlled from a transmitter 50 located, e.g., in the acupuncture office (not shown) via an RF receiver 52 installed on the generator assembly 40.

Figure 2:
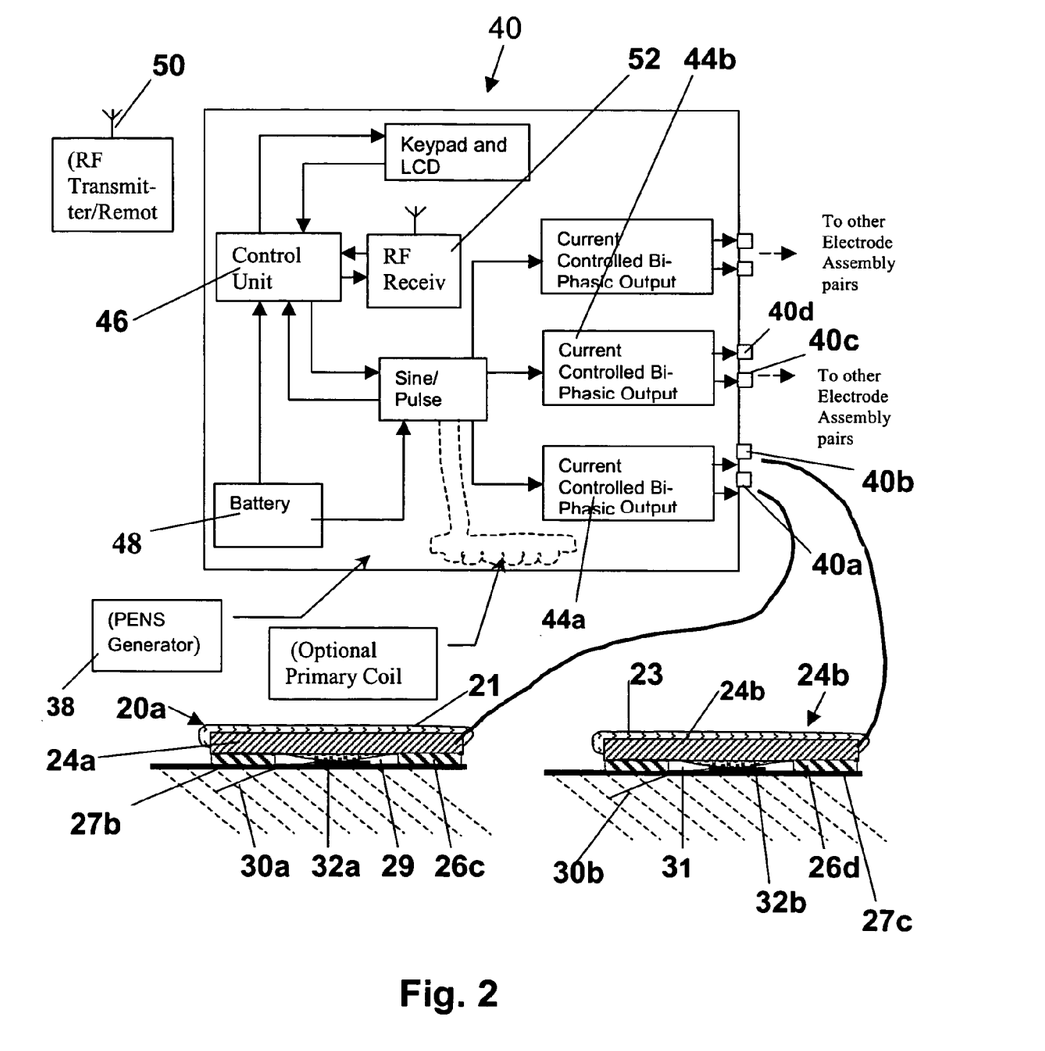
FIG. 2 is a block diagram of the entire electro-acupuncture apparatus or system according to one embodiment of the invention.

In the use of the electro-acupuncture apparatus according to the embodiment of FIG. 2, the electro-stimulating current flows from the pulse-generator 42 via the current-controlled bi-phasic output 44a, terminals 40a, 40b, and lead wires 34a, 34b to respective conductive pads 24a and 24b, and to the patient's tissue via the needles 30a and 30b. The electric circuit is then closed by a flow of the current through the patient's tissue from one needle to the other.

Figure 3:
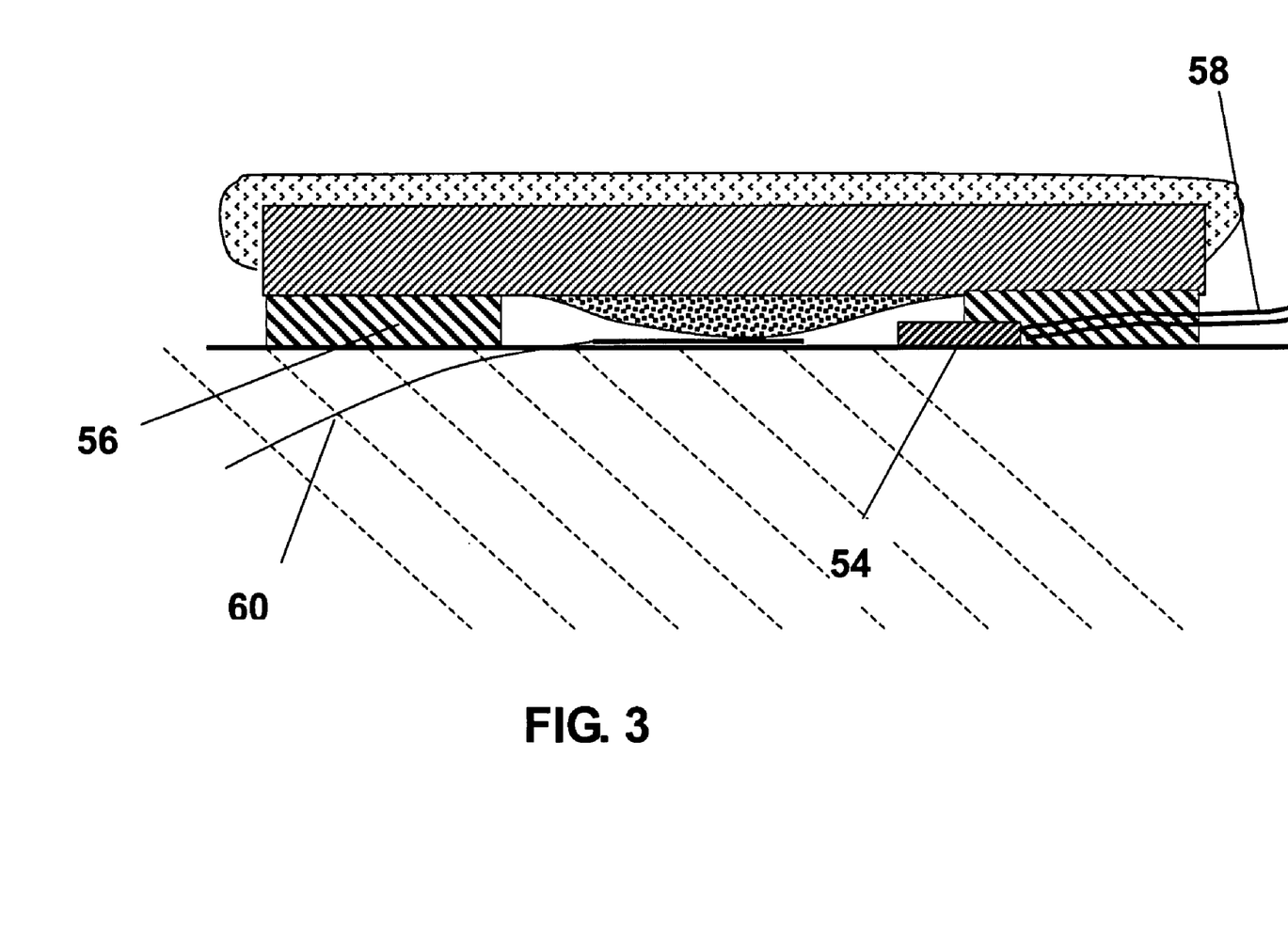
FIG. 3 is a view similar to FIG. 1 illustrating an electrode assembly that contains a tensor meter.

FIG. 3 shows another embodiment of the electrode assembly, which essentially is the same as the one shown in FIG. 1 and differs from it by a provision of a tensor meter 54 installed, e.g., under the insulation pad 56. The tensor meter 54 may be connected via feedback lead wire 58, e.g., to the control unit 46 (FIG. 2). The tensor meter 54 is used for measuring a change in muscle tension around the needles 60 (FIG. 3) in order to decrease the intensity of the electrical stimulation when tension increases. For example, when patient is trying to change his/her position from sitting to standing the electrical current should decrease.

Figure 4:
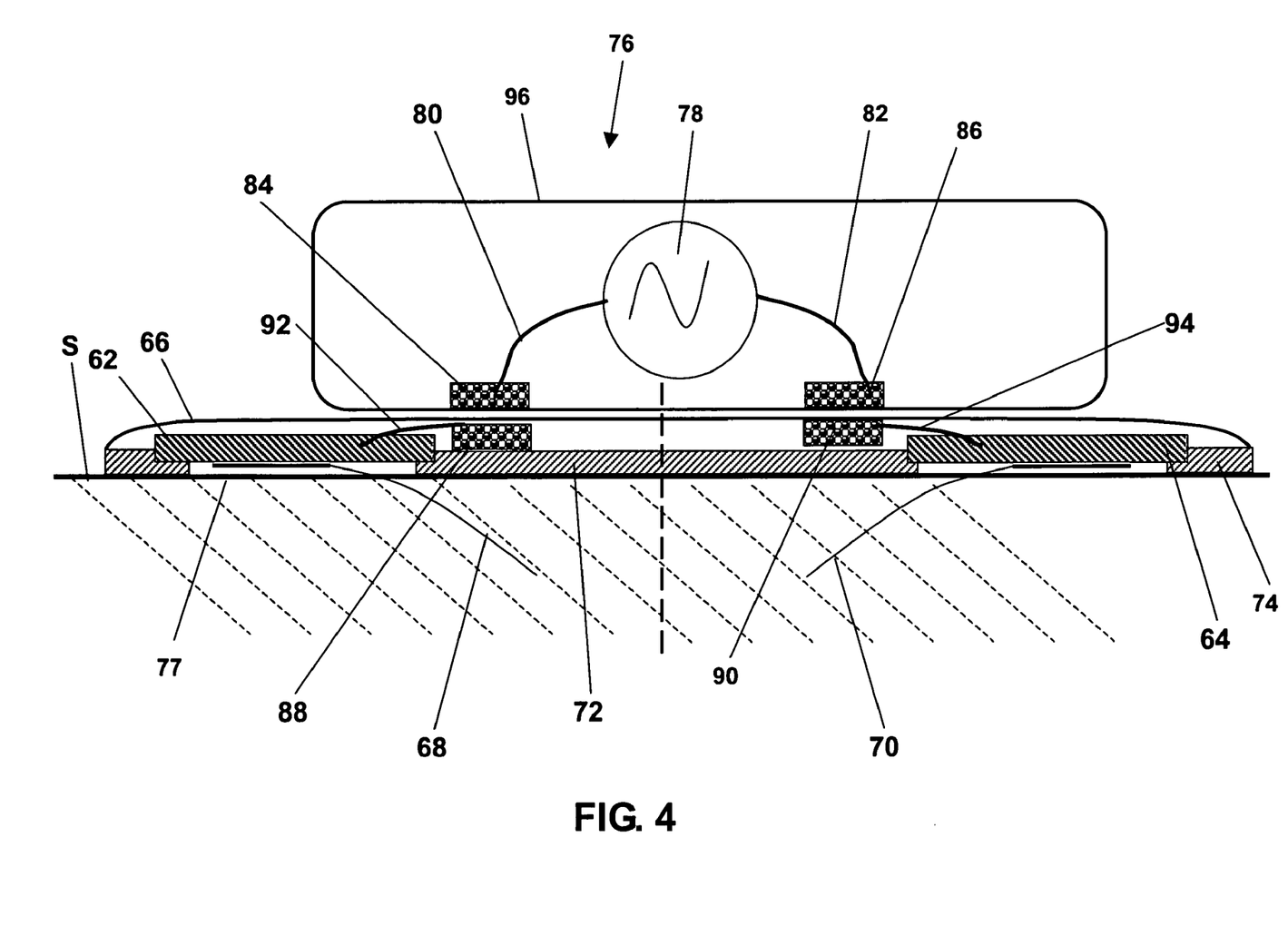
FIG. 4 is a sectional view of an electrode assembly according to another embodiment, in which two electrode sub-assemblies are covered by the same protective enclosure.

FIG. 4 shows an embodiment of an electrode assembly 76 wherein both conductive pads 62 and 64 are integrated into a single unit and covered by the same piece of the adhesive tape or enclosure 66. Similarly to the electrode assembly 20 of FIG. 1, the conductive pads 62 and 64 are in contact with respective needles 68 and 70. The conductive pads 62 and 64 are supported by an insulating pad 72 and by a circular sealing pad 74 that seals the electrode assembly 76 over its entire periphery, when the electrode assembly is attached to the patient's skin S. For attaching to the patient's skin, the bottom surface of the sealing pad 72 has an adhesive layer 77. The conductive pads 62 and 64 of this embodiment are electrically connected to a PENS generator 78 by lead wires 80 and 82 to respective primary coils 84 and 86 that inductively interact with secondary coils 88 and 90. The latter are supported by the insulating pad 72 and are electrically connected by lead wires 92 and 94 to the conductive pads 62 and 64, respectively. The PENS generator 78 and primary coils 84, 86 are encapsulated with an adhesive tape or enclosure 96.

Figure 5:
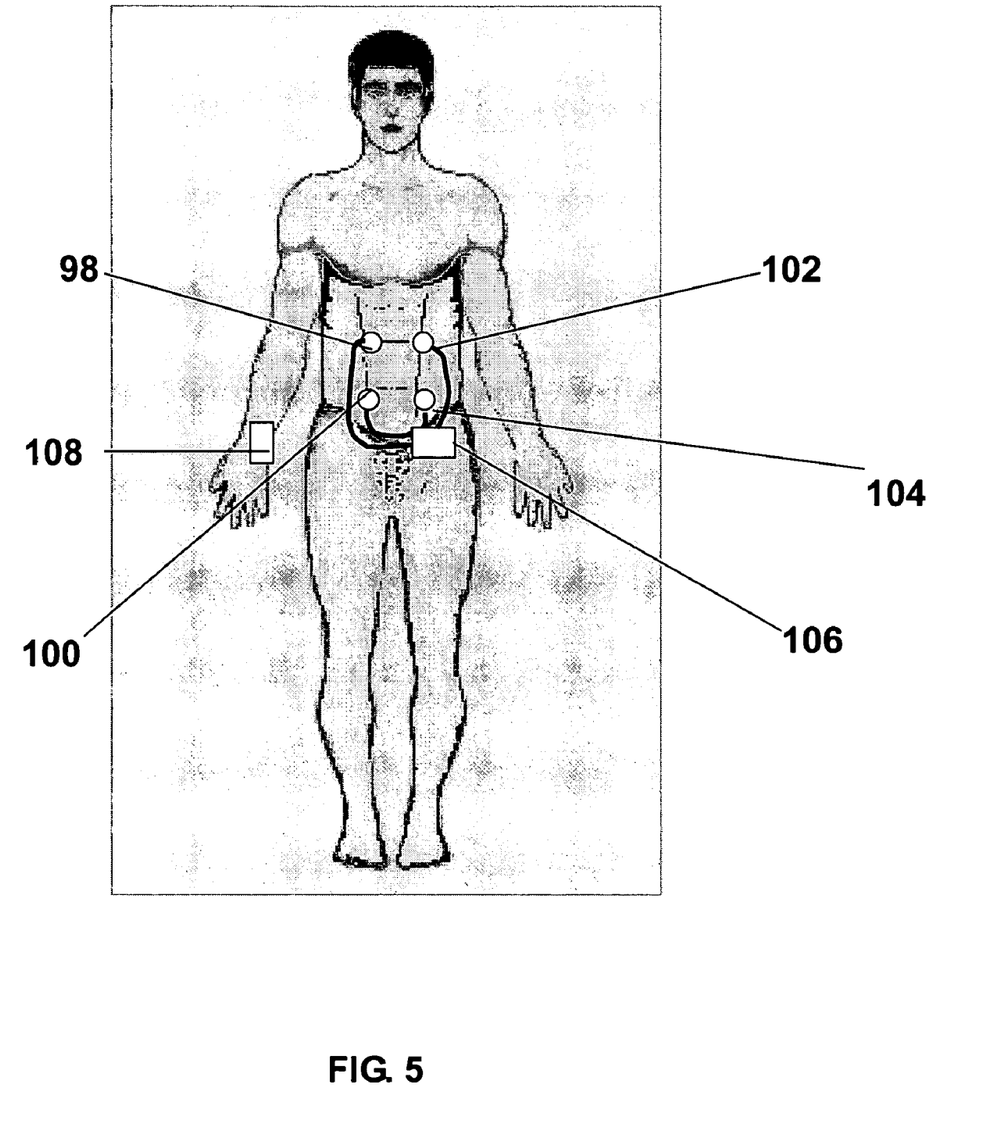
FIG. 5 is an example that illustrates arrangement of the components of the electro-acupuncture apparatus of the invention on the patient's body.

FIG. 5 shows two pairs of electrode assemblies, e.g., of the type shown in FIG. 1, that are attached to the patient's abdomen with the means described above. This assembly can be used for the treating, e.g., an irritable bowel syndrome. In FIG. 5, reference numerals 98, 100 and 102, 104 designate pairs of electrode assemblies, 106 is a PENS generator, and 108 is a remote control unit attached, e.g., to the patient's wrist for controlling operation of the apparatus, e.g., through a receiver/transmitter units 50, 52 shown in FIG. 2.

An inclined position of the needle/electrodes 30a and 30b provides a greater length of electrical contact between the current-carrying needle and the tissue of the patient's body, and thus ensures more efficient electro-stimulation.

A novel method of electro-acupuncture offered by the present invention consists in that a needle-electrode, e.g., the needle 30 of the electrode assembly 20 (FIG. 1), is introduced subcutaneous into patient's tissue at an acute angle to the patient's skin S, the portion 30b of the needle that obliquiely projects above the skin S is pressed in flush to the skin S by electro-conductive means, such as the electro-conductive pad 22 via a resilient electro-conductive means, such as the electro-conductive gel 32, the entire assembly is covered by a protective and insulating enclosure 24, and then the assembly is sealed over the periphery and secured to the patient's skin S, e.g., by an adhesive insulating pad 26 (FIG. 1) or with the use of a sealing pad 74.

Operation of the Device of the Invention

During the patient's initial visit to the doctor's office and after the differential diagnosis is established and specific points/areas are chosen for the electrical stimulation, at least two needles/electrodes, e.g., 30a and 30b shown in FIG. 2, are inserted at slant angles, e.g., of 5° to 45°, into the selected points on the patient's body. The external parts of the needles/electrodes are secured against the skin S in the order described below. First, the insulator pad 26c and 26d (FIG. 2) are attached to the skin S via their adhesive layers 27b, 27c.

Each ring-shaped insulator pad 26c and 26d (FIG. 2) has an opening 29 (31) in the middle. The insulator pad 26c and 26d encircle the area where the needle/electrodes 30a and 30b are inserted, but allow the external portion of the needle/electrodes to be accessible through the openings 29 and 31 in the pads 26c and 26d. Then, the conductive pads 24a and 24b, which are encapsulated within protecting insulating coverings 21 and 23 (FIG. 2) on all sides except the bottom where they are treated with conductive adhesive gel portions 32a and 32b, are placed on top of the insulator pads 26c and 26d. As a result, the conductive pads 24a and 24b get into contact with the respective needle/electrode 30a and 30b via the opening 29 and 31 in the insulator pads 26c and 26d.

The insulator pads 26c and 26d protect the skin S from electrical contact with the conductive pads 24a and 24b and improve comfort of the patient by minimizing an area in contact with conductive gel portions 32a and 32b. Electrical wires 34a and 34b then connect two conductive pads of the same pair of electrodes 20a and 20b (FIG. 2) with the portable PENS generator (40), as shown in FIG. 2. The portable PENS generator 40 is, then, secured on the patient's body, e.g., as shown in FIG. 5.

According to the embodiment shown in FIG. 4, the PENS generator 78 is encapsulated into the enclosing tape 96, which also contains primary electrical coils 84, 86. Secondary electrical coils are contained in the bottom tape/enclosure 66. The bottom tape/enclosure 66 is placed over the needles/electrodes 68, 70. The upper tape/enclosure 96 goes on top of the first one. In this embodiment (FIG. 4), the PENS generator 78 simply gets secured on the patient's body as a part of the upper enclosure/tape. The tapes/enclosures 66 and 96 are attached via the adhesives.

After the electrical circuit assembly, as shown in FIG. 2, is complete and the external portions of the needles, such as the needle head 30b (FIG. 1), are pressed against the patient's skin S and fixed in that position, the therapist makes sure that the patient's movements are unrestricted and that there is no discomfort from the inserted needles/electrodes, or from the adhesive tapes. At this moment the PENS procedure can be tested. The PENS unit is turned on, either by using the remote control 50, FIG. 2, or by a local switch (not shown). The electrical current starts flowing through the electrical wires, 34a and 34b, conductive pads 24a and 24b, into the needles/electrodes 30a and 30b, and through the tissues located between two needles/electrodes 30a and 30b. The current is slowly adjusted from low to high until the patient feels a tolerable amount of stimulation. The electrical parameters, which include intensity and frequency (usually 2 to 100 Hz) are selected according to the patient's diagnosis and his/her tolerance level and are tested while the patient is still in the office. The patient is instructed how to use the device or system away from the office and how to remove the needles/electrodes when desired. As in an assembled state the height "h" (FIG. 1) of the electrode assembly 20 over the patient's skin does not exceed 8 mm, the patient does not experience any restriction of movements while carrying the device on his/her body.

Alternatively, the patient is offered to come back to the office after certain period of time, say, by the end of the same day, after having used the device at work for a number of hours on and off, and to have it removed by a health care provider. The portable electro-acupuncture device of the invention is capable of providing multiple therapeutic PENS sessions in a course of one day for the same patient in order to control pain without extra participation of a health care provider. The number of the therapeutic sessions and their modes, such as the intensity of the electrical current, frequency, and duration of each session can be pre-programmed by a therapist or controlled manually by the patient according to the patient's needs.

Figure 6:
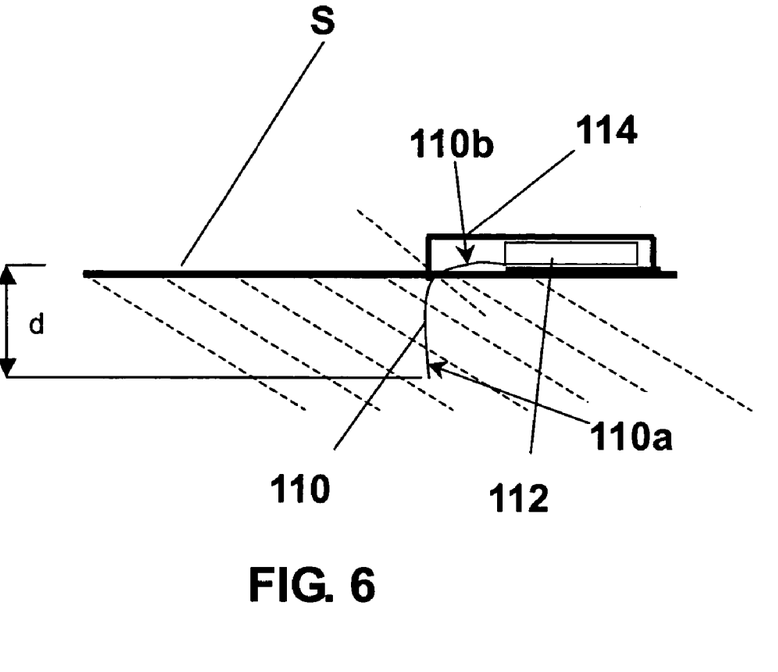
FIG. 6 illustrates an embodiment of the invention with an L-shaped needle.

FIG. 6 is a simplified schematic view of an electrode assembly which differs from the previous embodiments in that the needle/electrode 110 has an L-shaped configuration and consists of two perpendicular parts 110a that is inserted into the patient's skin S to its full depth "d" required for treatment and an external part 110b that is arranged in flush with the patient's skin S. Reference numeral 112 designates a conductive pad, and reference numeral 114 designates a protective isolating cover. The remaining components of the electrode assembly may be the same as described in the previous embodiments.

Figure 7:
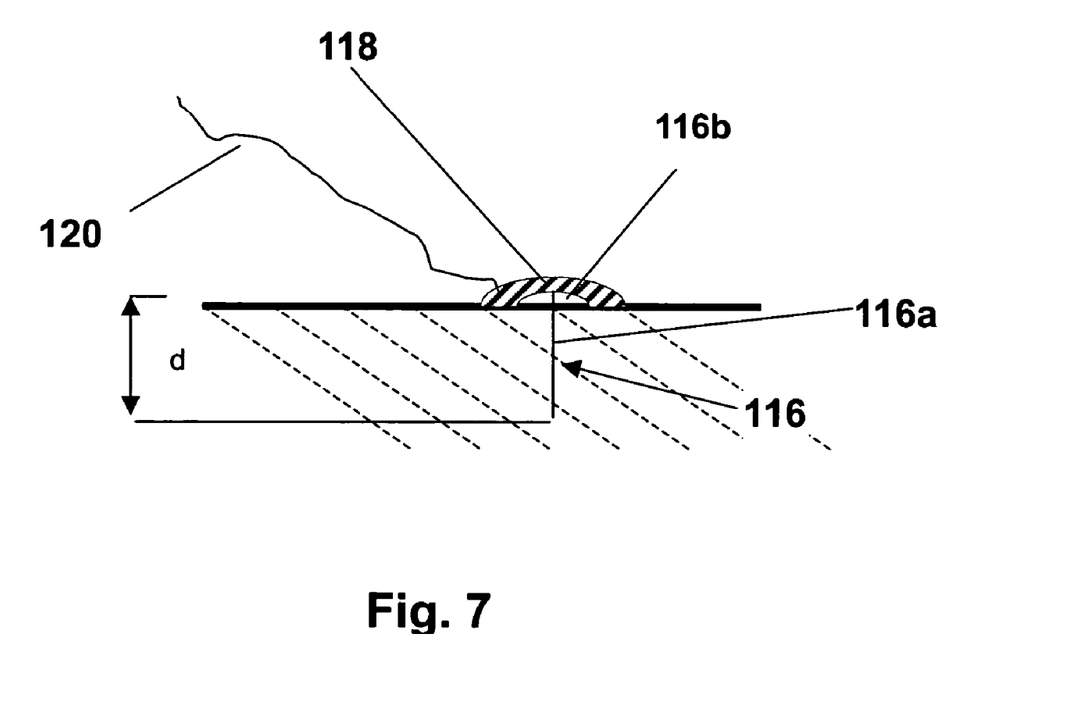
FIG. 7 is an embodiment of the invention with a button-shaped needle.

FIG. 7 shows another simplified embodiment of the electrode assembly that consists of a button-type needle/electrode 116 having an insertable portion 116a and a semispherical head 116b. The latter is covered by a semispherical protective insulating cap 118. Reference numeral 120 designates a lead wire connected to an electric pulse generator (not shown in FIG. 7).

Thus, it has been shown that the present invention provides a principally different method and a device for percutaneous electrical nerve stimulation and electro-acupuncture which are safer, less expensive, easy in use, and provides a patient with a higher level of control over his/her pain than known devices and methods of similar type. The invention also provides the aforementioned method and device that allow arranging and fixing the needles/electrodes in flash with the patient's skin so that the patient has freedom of movements and is not bound to the clinic during prolonged usage of the device, as well as for removal of the needles/electrodes.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For examples, the insulator pad can be integrated with the conductive pad and can cover the contact surface of the conductive pad along the periphery. The electrode assembly may have a shape different from circular. The conductive gel 32 (FIG. 1) can be replaced by a resilient conductive insert such a graphite-filled rubber or plastic block, etc.

The invention claimed is:

1. An electro-acupuncture device for treating a patient with acupuncture under conditions of electro-stimulation, said electro-acupuncture device comprising:
at least two electrode assemblies and an electric pulse generator electrically connected to said at least two electrode assemblies;
each of said at least two electrode assemblies comprising:
an electro-conductive needle/electrode that has an insertable portion that is to be subcutaneously inserted into the patient's tissue during the use of said electro-acupuncture device and an external portion that is maintained during the use of said electro-acupuncture device in flush with the surface of the patient's skin;
means for pressing said external portion of said electro-conductive needle/electrode to the patient's skin;
electro-conductive means for electrically connecting said external portion of said electro-conductive needle/electrode to said electric pulse generator;
protective means that isolate and cover each of said at least two electrode assemblies, and
attachment means that attach said at least two electrode assemblies to the patient's skin.

2. The electro-acupuncture device according to claim 1, wherein said electro-conductive needle/electrode has an insertable portion that during the use of said electro-acupuncture device is subcutaneously inserted into the patient's tissue and an external portion that is not inserted into the patient's tissue, said electro-conductive needle/electrode being selected from the group consisting of a straight needle/electrode that possesses flexibility and an L-shaped needle/electrode, in which said external portion is perpendicular to said insertable portion.

3. The electro-acupuncture device according to claim 2, wherein the length of said insertable portion of said L-shaped needle/electrode has a length that corresponds to the depth of insertion of said insertable portion in to the patient's tissue required for treatment and wherein said external portion is perpendicular to said insertable portion and is supported by the patient's skin when said insertable portion is inserted into the patient's tissue to said depth.

4. The electro-acupuncture device according to claim 2, wherein during the use of said electro-acupuncture device said straight needle/electrode is inserted into the patient's tissue at an acute angle so that a projecting part of said electro-conductive needle/electrode remains over the patient's skin in an oblique position with respect thereto.

5. The electro-acupuncture device of claim 4, wherein said electro-conductive means comprise an electro-conductive pad electrically connected to said external portion of said electro-conductive needle/electrode and to said electric pulse generator, said electro-conductive pad having one side that during the use of said electro-acupuncture device faces the patient's skin and another side that faces said protective means.

6. The electro-acupuncture device of claim 5, wherein said attachment means comprise an insulating pad attached to said one side of said electro-conductive pad and is provided with an adhesive layer for attachment to the patient's skin.

7. The electro-acupuncture device of claim 6, wherein said means for pressing said external portion comprises an electro-conductive gel placed between said external portion of said electro-conductive needle/electrode and said one side of said electro-conductive pad.

8. The electro-acupuncture device of claim 6, wherein said protective means comprises an insulating enclosure that covers each of said two electrode assemblies.

9. The electro-acupuncture device of claim 5, wherein said means for pressing said external portion comprises an electro-conductive gel placed between said external portion of said electro-conductive needle/electrode and said one side of said electro-conductive pad.

10. The electro-acupuncture device of claim 9, wherein said protective means comprises an insulating enclosure that covers each of said two electrode assemblies.

11. The electro-acupuncture device of claim 5, wherein said protective means comprises an insulating enclosure that covers each of said two electrode assemblies.

12. The electro-acupuncture device of claim 4, wherein said protective means comprises an insulating enclosure that covers each of said two electrode assemblies.

13. The electro-acupuncture device of claim 1, wherein said electro-conductive means comprise an electro-conductive pad electrically connected to said external portion of said electro-conductive needle/electrode and to said electric pulse generator, said electro-conductive pad having one side that during the use of said electro-acupuncture device faces the patient's skin and another side that faces said protective means.

14. The electro-acupuncture device of claim 13, wherein said attachment means comprise an insulating pad attached to said one side of said electro-conductive pad and is provided with an adhesive layer for attachment to the patient's skin.

15. The electro-acupuncture device of claim 14, wherein said means for pressing said external portion comprises an electro-conductive gel placed between said external portion of said electro-conductive needle/electrode and said one side of said electro-conductive pad.

16. The electro-acupuncture device of claim 14, wherein said protective means comprises an insulating enclosure that covers each of said two electrode assemblies.

17. The electro-acupuncture device of claim 13, wherein said means for pressing said external portion comprises an electro-conductive gel placed between said external portion of said electro-conductive needle/electrode and said one side of said electro-conductive pad.

18. The electro-acupuncture device of claim 17, wherein said protective means comprises an insulating enclosure that covers each of said two electrode assemblies.

19. The electro-acupuncture device of claim 13, wherein said protective means comprises an insulating enclosure that covers each of said two electrode assemblies.

20. The electro-acupuncture device of claim 1, wherein said protective means comprises an insulating enclosure that covers each of said two electrode assemblies.

21. The electro-acupuncture device of claim 1, wherein said protective means comprises an insulating enclosure that is common for said at least two electrode assemblies.

22. The electro-acupuncture device of claim 21, wherein each said electrode assembly comprises an electro-conductive needle/electrode that has an insertable portion that is to be subcutaneously inserted into the patient's tissue during the use of said electro-acupuncture device and an external portion that is maintained during the use of said electro-acupuncture device in flush with the surface of the patient's skin, a primary coil located on the outer side of said insulating enclosure and electrically connected to said electric pulse generator and a secondary coil that is located under said insulating enclosure, said secondary coil being inductively connected to said primary coil and being electrically connected to said electro-conductive means; said attachment means comprising an insulating pad attached to said one side of said electro-conductive pad and provided with an adhesive layer for attachment to the patient's skin, said insertable portion of said electro-conductive needle/electrode being inserted into the patient's tissue during the use of said electro-acupuncture device at an oblique angle to the patient's skin.

23. The electro-acupuncture device of claim 22, wherein said electro-conductive means comprise an electro-conductive pad electrically connected to said external portion of said electro-conductive needle/electrode and to said electric pulse generator, said electro-conductive pad having one side that during the use of said electro-acupuncture device faces the patient's skin and another side that faces said protective means.

24. The electro-acupuncture device of claim 23, further provided with a protective cover that encloses said electric pulse generator, and said primary coils of said first electrode assembly and said second electrode assembly.

25. The electro-acupuncture device of claim 23, further provided with an insulating pad that supports said electro-conductive pad said secondary coil of each of said electrode assemblies.

26. The electro-acupuncture device of claim 23, wherein said insulating enclosure is provided with sealing means over periphery of said insulating enclosure, said sealing means having an adhesive layer for securing said electro-acupuncture device to the patient's skin.

27. The electro-acupuncture device of claim 22, further provided with a protective cover that encloses said electric pulse generator, and said primary coils of said first electrode assembly and said second electrode assembly.

28. The electro-acupuncture device of claim 27, wherein said insulating enclosure is provided with sealing means over periphery of said insulating enclosure, said sealing means having an adhesive layer for securing said electro-acupuncture device to the patient's skin.

29. The electro-acupuncture device of claim 22, wherein said insulating enclosure is provided with sealing means over periphery of said insulating enclosure, said sealing means having an adhesive layer for securing said electro-acupuncture device to the patient's skin.

30. The electro-acupuncture device of claim 21, wherein said insulating enclosure is provided with sealing means over periphery of said insulating enclosure, said sealing means having an adhesive layer for securing said electro-acupuncture device to the patient's skin.

31. A method for treating a patient with acupuncture in combination with electrostimulation comprising the steps of:
  providing a portable electro-acupuncture device that can be attached to the patient's body, said device comprise at least a pair of electrode assemblies with an electro-conductive needle-electrode in each of said electrode assemblies and a common electric pulse generator electrically connected to said electro-conductive needle-electrode of each of said electrode assemblies;
  inserting said electro-conductive needle-electrode of each of said electrode assembly subcutaneously into the patient's tissue at an acute angle to the patient skin;
  pressing on said external portion of each of said conductive needle-electrode of each of said electrode assemblies for positioning said external portion in flush with the patient's skin;
  securing said external portion in said position in flush with the patient's skin;
  covering said electrode assemblies with a protective insulating enclosure; and
  securing said portable electro-acupuncture device on the patient's body in a position that provides the patient with freedom of movements.

* * * * *